(12) United States Patent
Weinberg

(10) Patent No.: US 10,888,699 B2
(45) Date of Patent: Jan. 12, 2021

(54) HIGH-RESOLUTION BRAIN MACHINE INTERFACE WITH MAGNETICALLY-RESPONSIVE ARRAY SWITCHES COUPLED TO AN INTERNAL ANTENNA

(71) Applicant: Weinberg Medical Physics, Inc., North Bethesda, MD (US)

(72) Inventor: Irving N. Weinberg, North Bethesda, MD (US)

(73) Assignee: Weinberg Medical Physics, Inc.

( * ) Notice: Subject to any disclaimer, the term of this patent is extended or adjusted under 35 U.S.C. 154(b) by 0 days.

(21) Appl. No.: 15/669,036

(22) Filed: Aug. 4, 2017

(65) Prior Publication Data

US 2018/0036532 A1 Feb. 8, 2018

Related U.S. Application Data

(60) Provisional application No. 62/371,932, filed on Aug. 8, 2016.

(51) Int. Cl.
*A61N 1/36* (2006.01)
*A61N 1/372* (2006.01)
*A61N 1/05* (2006.01)
*A61N 2/00* (2006.01)
*A61N 1/378* (2006.01)

(52) U.S. Cl.
CPC ....... *A61N 1/3606* (2013.01); *A61N 1/37223* (2013.01); *A61N 1/0529* (2013.01); *A61N 1/3787* (2013.01); *A61N 1/37205* (2013.01); *A61N 2/006* (2013.01)

(58) Field of Classification Search
CPC ............... A61N 1/0529; A61N 1/3606; A61N 1/37205; A61N 1/37223; A61N 1/3787; A61N 2/006
See application file for complete search history.

(56) References Cited

U.S. PATENT DOCUMENTS

2014/0206927 A1* 7/2014 Weinberg ........... A61B 18/1206
600/9

* cited by examiner

*Primary Examiner* — Eric D. Bertram
(74) *Attorney, Agent, or Firm* — Barnes & Thornburg LLP

(57) ABSTRACT

A neuronal tissue-machine interface apparatus includes an array of magnetically-responsive switches positioned in close proximity or contact to neuronal tissue of a human subject, wherein a magnetic environment of the plurality of magnetically-responsive switches varies along the array, and an antenna that is electrically connected to the array, wherein a subset of the magnetically-responsive switches respond to electromagnetic energy received by the antenna, and wherein the response of the subset of the magnetically-responsive switches includes modulation of an electrical current conducted by the subset of the magnetically-responsive switches.

10 Claims, 3 Drawing Sheets

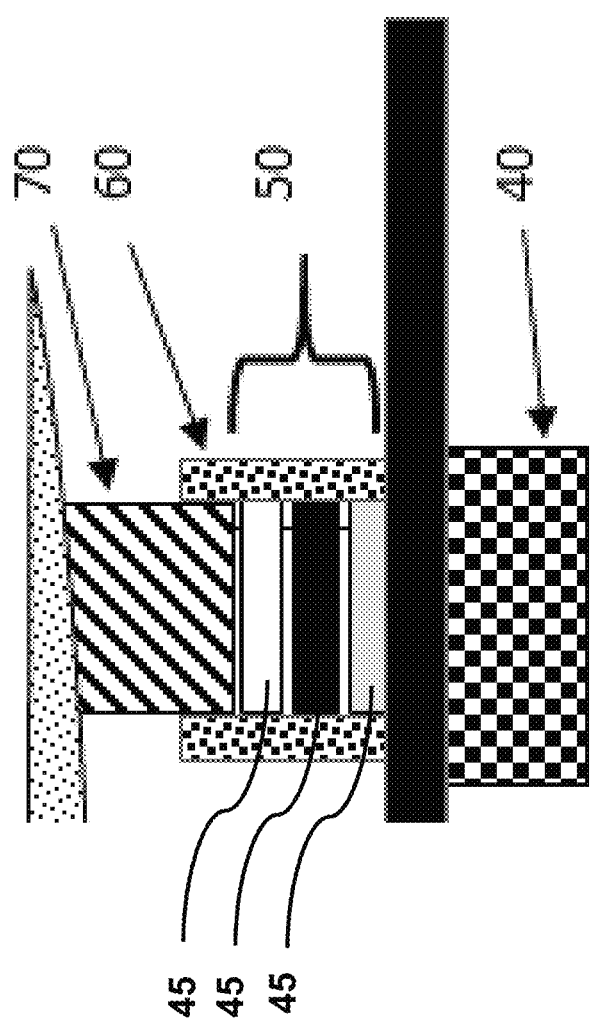

HIGH-RESOLUTION BRAIN MACHINE INTERFACE WITH MAGNETICALLY-RESPONSIVE ARRAY SWITCHES COUPLED TO AN INTERNAL ANTENNA

CROSS-REFERENCE TO RELATED APPLICATIONS

This application relies for priority on U.S. Provisional Patent Application Ser. No. 62/371,932, entitled "HIGH-RESOLUTION BRAIN MACHINE INTERFACE WITH MAGNETICALLY-RESPONSIVE ARRAY SWITCHES COUPLED TO AN INTERNAL ANTENNA," filed on Aug. 8, 2016, the entirety of which being incorporated by reference herein.

FIELD

Disclosed embodiments are directed, generally, to a brain-machine interface capable of projecting electrical currents and/or voltages to a living brain with high spatial and temporal resolution.

BACKGROUND

Existing brain-machine interfaces suffer from limited bandwidth, spatial resolution, and size.

SUMMARY

Disclosed embodiments are directed to a brain-machine interface capable of projecting electrical currents and/or voltages to a living brain with high spatial and temporal resolution.

BRIEF DESCRIPTION OF THE FIGURES

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

FIG. 3 illustrates additional detail regarding the magnetically-responsive switches illustrated in FIG. 1.

DETAILED DESCRIPTION

The description of specific embodiments is not intended to be limiting. To the contrary, those skilled in the art should appreciate that there are numerous variations and equivalents that may be employed without departing from the scope of the present invention. Those equivalents and variations are intended to be encompassed by the present invention.

In the following description of various embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention. Furthermore, it should be understood that the term "subject" refers to any of various organisms having a brain organ, in particular, a human being, whether alive or dead, conscious or unconscious.

Moreover, in accordance with at least one embodiment various connections are set forth between elements in the following description; however, these connections in general, and, unless otherwise specified, may be either direct or indirect, either permanent or transitory, and either dedicated or shared, and that this specification is not intended to be limiting in this respect.

Figure 1:
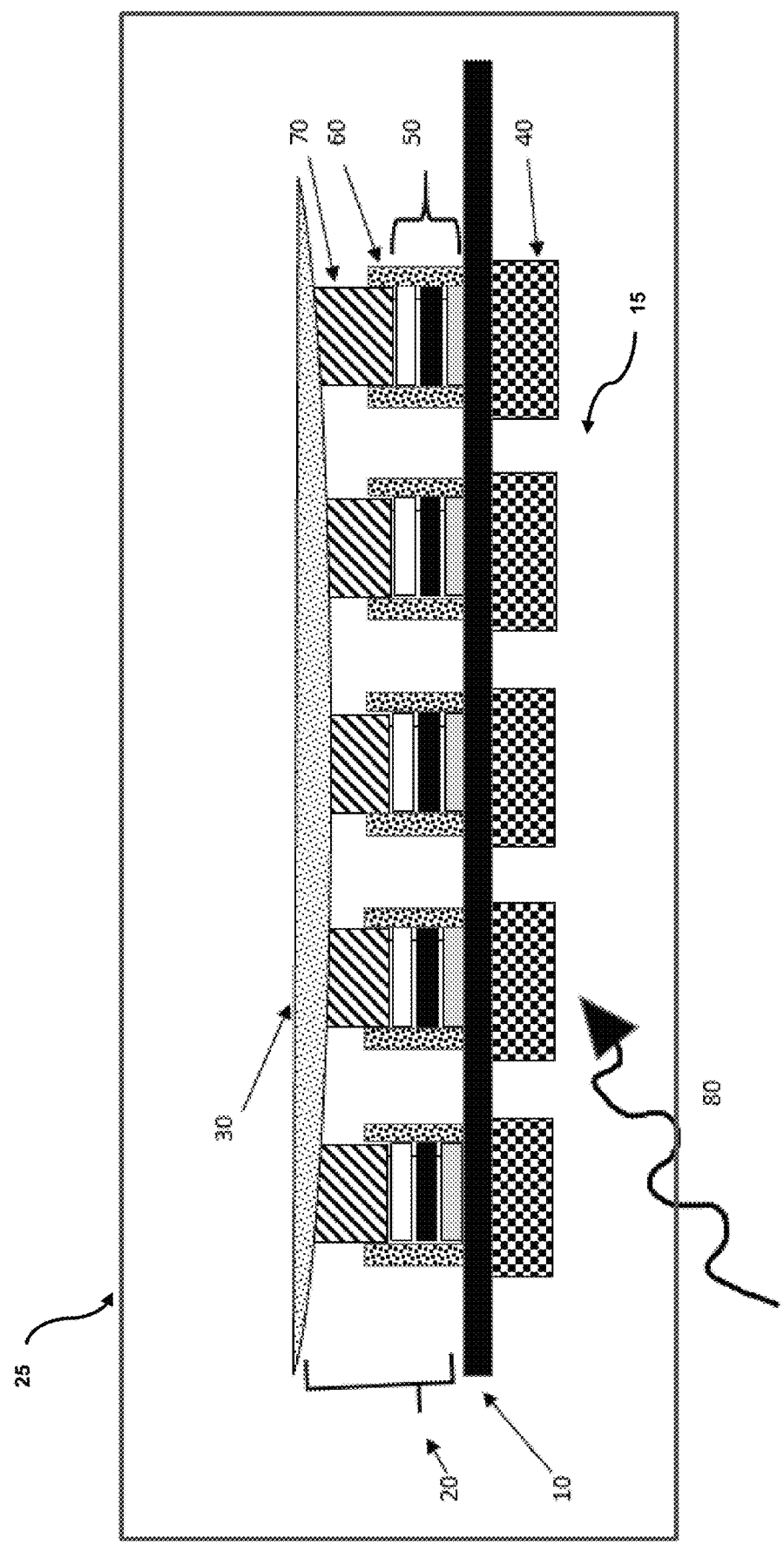
FIG. 1 illustrates an exemplary embodiment wherein an apparatus includes an electrical backplane antenna internal to a subject's body, in which the internal antenna consists of one or more conductive paths.

FIG. 1 illustrates an exemplary embodiment a system using a high-resolution brain machine interface wherein an apparatus 15 includes an electrical backplane antenna 10 internal to a subject's body 25, in which the internal antenna 10 includes one or more conductive paths via the electrical contacts 7 in close proximity and/or in contact with neuronal tissue. As shown in FIG. 1, an array 20 of microscopic magnetically-responsive switches 50 is provided and positioned in electrical contact with backplane antenna 10, so that electrical energy delivered to the backplane antenna 10 is available to the array 20.

For the purposes of this disclosure, the term "microscopic magnetically-responsive switch" refers to and includes at least a structure having a length less than ten microns in at least one dimension, and which contains one or more materials that respond to ambient magnetic fields to modulate or convert an electrical current passing through the switch. Examples of magnetically-responsive switches 50 include spin transfer nano-oscillators, vortex spin polarizers, and magneto-electric assemblies.

The array 20 of microscopic magnetically-responsive switches 50 may be spintronic switches. A spintronic device includes layers of magnetizable and other materials (generally in a sub-micron-sized assembly) which can modulate a current under the influence of applied electromagnetic fields. An example of spintronic devices applied to sampling brain electrical activity is disclosed in U.S. patent application 61/810,436 by Irving Weinberg, entitled "Neuroparticle," incorporated herein by reference".

At least one of the microscopic magnetically-responsive switches 50 in the array 20 is in close physical contact with the subject's brain or other neuronal tissue 30. For example, the neuronal tissue 30 may be a portion of the brain cortex, or of a neuron in the periphery of the body, or a neuron in another organ such as the heart or intestine.

An array of magnetizable materials 40 is shown in proximity to backplane 10. An example of the magnetically-responsive switches 50 in array 20 is illustrated as a set of layers 45, as illustrated in FIG. 3, at least some of which layers are magnetizable. An electrically-insulating sheath 60 is shown surrounding some portion of the magnetically-responsive switch 50.

As shown in FIG. 1, an electrical contact 70 is connects or couples the magnetically-responsive switch 50 to the neuronal tissue 30. Through operation of the apparatus, as described herein, incident energetic radiation 80 strikes the backplane 10 and potentiality other portions of the apparatus 15.

Figure 2:
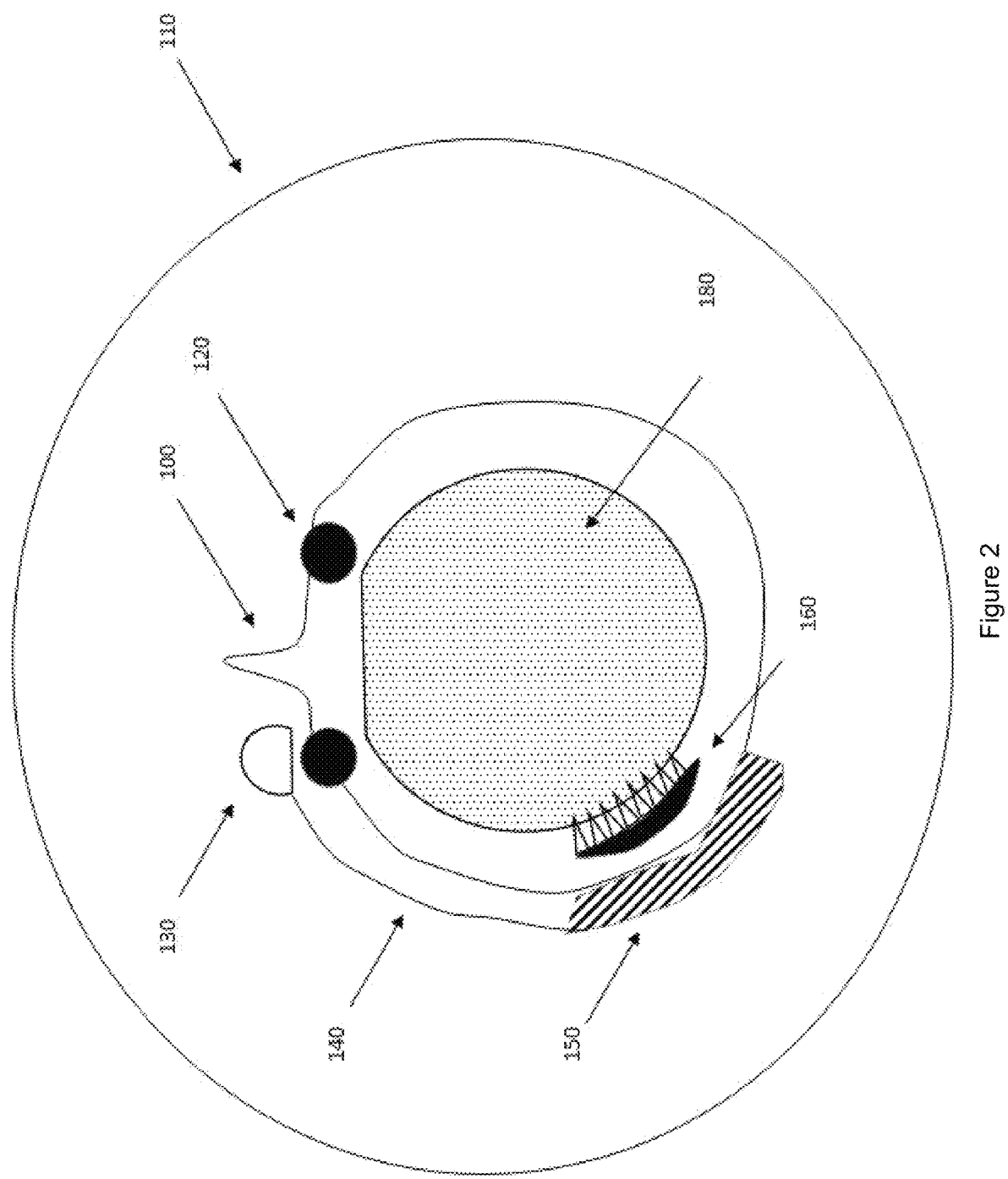
FIG. 2 illustrates a configuration of the exemplary embodiments that may be implemented to restore sight to a subject.

FIG. 2 illustrates a configuration of the disclosed embodiments that may be implemented to restore sight to a subject whose head 100 is lying in a magnetic field generator 110.

One or both of the subject's eyes 120 have been damaged. As shown in FIG. 2, digital camera 130 is provided and includes constituent electronics and computing capability (not shown) conventionally understood within the state of the art. A cable or other connector 140 may connect the output of camera 130 to an antenna 150 on the scalp of the subject. Although not illustrated, one or more power sources may be positioned on the scalp or body of subject 100 to power the antenna 150 and set its frequency or frequencies. Antenna 150 transmits a signal to the array 20 described in connection with FIG. 1, and whose electrical contacts touch the subject's brain 180.

Although illustrated in two dimensions in FIG. 2, in accordance with at least one embodiment, the antenna 150 and array 160 may be three-dimensional structures, and can vary in shape and electromagnetic properties along any or all of the three dimensions.

In operation, at least one embodiment applies a magnetic gradient to the apparatus, so that magnetizable components retain magnetizations with different strengths and/or directions with respect to one another. In one of various implementations, the magnetic gradient may be applied from outside a body part of the subject in which the apparatus has been inserted. For example, if the apparatus is inserted on the surface of the human cortex, then the magnetic gradient may be applied by a set of electromagnets and/or permanent magnets outside the subject's head as in FIG. 2.

Returning to FIG. 1, as part of operation of the apparatus, an energetic wave 80 may be generated from outside the body of a human subject in which the apparatus 15 is positioned. It is understood that energetic wave 80 may be electrical or magnetic or acoustic or a combination of these or other forms of energy. At least one frequency of the electromagnetic wave 80 is selected by a controller (e.g., hardware and software configured to control generation of one or more energy waves) to modulate, e.g., control activation of at least one magnetically-responsive switch 50 in the array 20.

An example of such modulation may be that the switch 50 conducts electrical current and/or voltage through contact 70 into neuronal tissue 30 of the human subject. Another form of modulation may be the delivery of kinetic or light energy to neuronal tissue 30. Kinetic modulation could be accomplished through magnetic attraction of one contact to another as a result of currents carried through the contacts. Light energy modulation could be accomplished through electrical activation of a light emitting diode at the contact. Additionally, the modulation effected by switch 50 can convert a high frequency electrical signal from wave 80 into a low-frequency signal that can stimulate neuronal tissue 30.

In accordance with at least one embodiment, contacts 70 may be separate components from switches 50, as shown in FIG. 1, or may be a part of each switch 50. The modulation of switches 50 is controlled based on the energy delivered by the energetic wave 80. As such, control of the activation of each of the plurality of switches 50 may be controlled based on, for example, a frequency of the energetic wave; additionally, the modulation of the switches 50 may be controlled as increased electrical conductance, or may be rectification of the waveform of energetic wave 80. It is understood that the rectification can result in transformation of the high frequency electromagnetic signal received by the antenna 10 into a low-frequency signal that can stimulate the neurons in the neuronal tissue 30. Insulating layer 60 may serve to isolate or more of the constituent components of magnetically-responsive switches 50.

Although energy is shown being delivered to the backplane 10 by an energetic wave 80 with origin outside the neuronal tissue 30, an alternative embodiment (or an additional option for the previously disclosed embodiment) would be for energy to be delivered to backplane 10 from a battery or other power source in or near the neuronal tissue. An example of such a power source would be a fuel cell powered by glucose and capable of supplying electrical power. An example of such a fuel cell was provided by Lamar Mair in his U.S. Patent Application No. 62/606,8083, entitled "SCALABLE, MASSIVELY PARALLEL PROCESS FOR MAKING MICRO-SCALE PARTICLES THAT INCORPORATE A FUEL CELL", and incorporated herein by reference.

By generating and controlling application of a heterogeneous magnetic field on the array 20 of magnetically-responsive switches 50 using the energetic wave 80, the disclosed embodiments may be used to spatially select a location in the neuronal tissue 30 to receive electrical current as a result of modulation of one or more switches 50 in the array 20. In implementation, it is understood that one or more magnetically-responsive switches 50 may be sensitive to the polarization of incident energy wave 80. This sensitivity may be conferred as a result of the constituent materials 45 used in each of the magnetically-responsive switches 50. Alternatively, or in addition, the backplane antenna 10 may be configured so that one polarization is more likely to be effective at energizing some switches 50 of switch array 20 than other switches 50 of array 20, or through a combination of these factors.

In accordance with at least one embodiment, the combination of locally-variant magnetic environments which affect the frequency to which the magnetically-responsive switches respond and the degree and orientation of polarization of the incident energy provides the ability to preferentially select among a subset of a plurality of switches 50 in the array 20.

For example, consider the example wherein incident energy of the energetic wave 80 has a carrier frequency of 2 GHz, and the linewidth of a spin vortex switch is 100 kHz, and a switch 50 is preferably responsive to one circular polarization, wherein each switch 50 in an array is 10-microns from the next switch. The term "preferably responsive" is intended to mean that the switch will require a lower threshold of activation for electromagnetic waves that impinge of the switch with a certain circular polarization. Based on such a configuration, the array 20 may effectively stimulate neuronal tissue with a spatial resolution of 10-microns along an area of 20,000 by 20,000 pixels.

In accordance with at least one embodiment, the stimulation of neuronal tissue 30 may be effected as a result of physical motion of magnetically-responsive switches 50, as could occur, for example, if the switches 50 were made of magneto-electric materials, for example, a combination of piezoelectric and magnetic components.

In accordance with at least one embodiment, the magnetic configuration state of magnetizable materials 40 used in the switches 50 may change over time, as a result of decay and/or through administration of external magnetic fields and other mechanisms.

In accordance with at least one embodiment, the backplane antenna 10 efficiently couples radiation from the external antenna 150 because microscopic switches are otherwise inefficient at collecting radiation. A typical frequency of such radiation may be in the range of 0.1 to 10 GHz, and may be selected (using the software and hardware discussed above) from within this range so as to be readily transmitted through tissue of a human subject's body without significant heating, while providing high bandwidth. This high bandwidth can be used to implement rapid transmission and high temporal resolution. It is known that the neuron fires with a rate on the order of 10 Hz, so that an assembly of millions of neurons should preferably have a bandwidth exceeding 10 MHz.

In accordance with the disclosed embodiments, use of the disclosed apparatus and operations may be implemented to address various different medical issues related to neuronal tissue's interaction with other parts of a human subject's body. For example, as illustrated in FIG. 2, a human subject with visual deficits may be surgically operated upon to insert an apparatus in accordance with the disclosed embodiments upon the surface of the brain cortex. A magnetic field may then be applied by a machine external to the body 110, in order to set magnetizable material 40 (illustrated in FIG. 1) to different field strengths and set directions so that each of the plurality of switches 50 (also illustrated in FIG. 1) are addressable in small numbers (e.g., less than ten), and optionally, individually. Once configuration of the magnetizable material 40 is completed so that magnetic directions and strengths for the switches 50 are established, the magnetic field used to set these characteristics may be discontinued.

In implementation, it should be understood that the machine 150 used to generate and apply the magnetic field(s) used to set or establish these characteristics may be, for example, a system with fast-rising magnetic fields that do not cause unintended bio-effects, as disclosed by Irving Weinberg in U.S. patent application Ser. No. 12/905,256, entitled "Apparatus and Method for Decreasing Bioeffects of Magnetic Gradient Field Gradients" and related disclosures, incorporated herein by reference. Thus, in such a configuration, following establishment of the characteristics, a human subject may leave the machine 110.

Thereafter, the human subject may be fitted with a cap, helmet or other appliance or device 105 upon or near his or her head 100. That device 105 may include components and be coupled to equipment configured to enable emission of radiofrequency electromagnetic radiation with frequencies, amplitudes, and/or polarizations selected and controlled one or more computers and/or data processing devices based at least in part on input from one or more sensors 130, e.g., a digital camera.

In operation, the emitted radiation excites a subset of the plurality of switches 50 in array 20 so as to stimulate brain 180 in order to enable the human subject to perceive an image as collected by sensors 130.

In accordance with at least one embodiment, the one or more of switches 50 included in the array 20 can also operate in the reverse direction, so as to transmit electrical energy from neuronal surface 30 to backplane 10 and thereby to antenna 150 for reception of neuronal signals as a two-way brain-machine interface. Further, in accordance with at least one embodiment, the magnetically-responsive switches may act coherently, in cooperation, in order to boost such transmitted signals.

Although FIG. 1 shows the magnetizable materials 40 as being separate from other components in the apparatus, it is understood that either the backplane 10 or magnetically-responsive switches 50, or a combination of these components may include magnetizable materials 40 so that a separate set of magnetizable materials 40 is not necessary for operation of the devices. In accordance with at least one embodiment, the magnetizable materials 40 may be on the same side of backplane 10 instead of on the other side as shown in FIG. 1, or may straddle backplane 10, and may not need to be in physical contact with backplane 10 as shown in FIG. 1.

It is understood that the term "neuronal" means tissue containing neurons and/or nerves, or nervous tissue, or receptors that interface with nerves (for example the rods of the eye).

In accordance with at least one embodiment, backplane 10 may in fact by composed of multiple antennas, which may or may not be connected to one another.

While disclosed embodiments have been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

Additionally, it should be understood that the functionality described in connection with various described components of various embodiments may be combined or separated from one another in such a way that the architecture of the resulting system is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

As a result, it will be apparent for those skilled in the art that the illustrative embodiments described are only examples and that various modifications can be made within the scope of the invention as defined in the appended claims.

What is claimed:

1. A neuronal tissue-machine interface apparatus comprising:
    an array of a plurality of magnetically-responsive switches positioned in close proximity or contact to neuronal tissue of a human subject, wherein a magnetic environment of the plurality of magnetically-responsive switches varies along the array; and
    an antenna that is electrically and physically connected to each of the plurality of magnetically-responsive switches, the antenna configured to transmit electromagnetic energy to activate each of the plurality of magnetically-responsive switches,
    wherein a subset of the plurality of magnetically-responsive switches respond to a frequency of the electromagnetic energy received by the antenna, and
    wherein the response of the subset of the plurality of magnetically-responsive switches includes modulation of an electrical current conducted by the subset of the plurality of magnetically-responsive switches.

2. The neuronal tissue-machine interface apparatus of claim 1, further comprising one or more sensors, wherein signals from the one or more sensors affect energy transmitted by the antenna so as to stimulate the neuronal tissue.

3. The neuronal tissue-machine interface apparatus of claim 2, wherein the signals from the one or more sensors are transmitted via a cable to an antenna positioned outside the body of the human subject.

4. The neuronal tissue-machine interface apparatus of claim 2, further comprising an antenna positioned outside the body of the human subject, wherein the signals from the one or more sensors are transmitted to the antenna positioned outside the body of the human subject.

5. The neuronal tissue-machine interface apparatus of claim 1, wherein the switches are spintronic devices.

6. The neuronal tissue-machine interface apparatus of claim 1, wherein the antenna directly contacts each of the plurality of switches.

7. A method for stimulating neuronal tissue with high spatial resolution, the method comprising:
 transmitting energy from outside a body of a human subject to an antenna positioned inside the body of the human subject,
 wherein the antenna is connected electrically and physically to magnetically-responsive switches that form an array, the antenna configured to transmit the energy to activate each of the magnetically-responsive switches in the array, whereby a magnetic environment of a subset of magnetically-responsive switches in the array is affected by delivering a frequency of the energy from outside the body to neuronal tissue in the human subject so as to activate the subset of magnetically-responsive switches,
 wherein the subset of magnetically-responsive switches conduct electricity upon activation by the frequency of the energy available from the antenna, and
 wherein such activated switches stimulate at least one section of the neuronal tissue.

8. The method for stimulating neuronal tissue of claim 7, wherein the form of the electromagnetic energy is at least one of electrical, magnetic, and acoustic.

9. The method for stimulating neuronal tissue of claim 7, further comprising using input from a controller to select a form of the electromagnetic energy transmitted from outside the body of the human subject to the antenna in the body of the human subject so that stimulated neuronal tissue is related to an input received by the digital sensor.

10. The method for stimulating neuronal tissue of claim 7, wherein the antenna directly contacts each of the magnetically-responsive switches.

* * * * *